(12) United States Patent
Dentinger et al.

(10) Patent No.: US 6,858,378 B1
(45) Date of Patent: Feb. 22, 2005

(54) PHOTOIMAGEABLE COMPOSITION

(75) Inventors: Paul Dentinger, Sunol, CA (US); Karen L. Krafick, Livermore, CA (US); Kelby Liv Simison, Hattiesburg, MS (US)

(73) Assignee: Sandia National Laboratories, Livermore, CA (US)

( * ) Notice: Subject to any disclaimer, the term of this patent is extended or adjusted under 35 U.S.C. 154(b) by 259 days.

(21) Appl. No.: 10/125,134

(22) Filed: Apr. 17, 2002

(51) Int. Cl.[7] .............................................. G03F 7/40
(52) U.S. Cl. .................. 430/324; 430/280.1; 430/914; 430/925; 430/325
(58) Field of Search ........................ 430/325, 280.1, 430/324

(56) References Cited

U.S. PATENT DOCUMENTS

| | | | |
|---|---|---|---|
| 4,550,128 A | * | 10/1985 | Chellis ........................ 523/433 |
| 4,882,201 A | * | 11/1989 | Crivello et al. .......... 430/280.1 |
| 4,940,651 A | * | 7/1990 | Brown et al. ............. 430/280.1 |
| 4,948,707 A | * | 8/1990 | Johnson et al. .............. 430/311 |
| 5,055,439 A | | 10/1991 | Allen et al. |
| 5,144,051 A | * | 9/1992 | Kessel et al. ................. 556/64 |
| 5,206,983 A | | 5/1993 | Guckel et al. |
| 5,260,349 A | * | 11/1993 | Crivello ....................... 522/31 |
| 5,378,583 A | | 1/1995 | Guckel et al. |
| 5,426,222 A | * | 6/1995 | Wargo et al. ................ 562/602 |
| 5,554,664 A | | 9/1996 | Lamanna et al. |
| 5,665,792 A | * | 9/1997 | Lawton et al. ................. 522/31 |
| 5,679,495 A | | 10/1997 | Yamachika et al. |
| 5,757,507 A | | 5/1998 | Ausschnitt et al. |
| 5,877,229 A | * | 3/1999 | Janke et al. .................. 522/31 |
| 5,998,099 A | | 12/1999 | Houlihan et al. |
| 6,090,474 A | * | 7/2000 | Johansson et al. .......... 428/209 |
| 6,096,484 A | | 8/2000 | Azuma |
| 6,103,447 A | | 8/2000 | Chen et al. |
| 6,128,067 A | | 10/2000 | Hashimoto |
| 6,146,810 A | | 11/2000 | Seo et al. |
| 6,153,349 A | | 11/2000 | Ichikawa et al. |
| 6,207,347 B1 | | 3/2001 | Lundy et al. |
| 6,210,862 B1 | | 4/2001 | Day et al. |
| RE37,179 E | | 5/2001 | Yamachika et al. |

(List continued on next page.)

FOREIGN PATENT DOCUMENTS

CA    2247777 A1 *  3/1999  ............. G03F/7/20

OTHER PUBLICATIONS

Johnson et al, 138:360305, CAPLUS, Copyright 2003 ACS on STN 2003:90468, Chemical Abstracts of Improving the process capability of SU–8, part III, Journal of Photopolymer Science and Technology (2002), 15(5), 749–756, Date publication Dec. 20, 2002.*

Shaw et al, "Negative photoresists for optical lithography", IBM J. Res. Develop., Vo. 41, No. 1/2, Jan./Mar. 1997, pp. 81–94.*

*Primary Examiner*—Cynthia Hamilton
(74) *Attorney, Agent, or Firm*—Fliesler Meyer LLP

(57) ABSTRACT

The use of photoacid generators including an alkoxyphenylphenyliodonium salt and/or bis(t-butylphenyl)iodonium salt in a photoimageable composition helps improve resolution. Suitable photoimageable compositions includes: (a) a multifuctional polymeric epoxy resin that is dissolved in an organic solvent wherein the epoxy resin comprises oligomers of bisphenol A that is quantitatively protected by glycidyl ether and wherein the oligomers have an average functionality that ranges from about 3 to 12; and a photoacid generator comprising an alkoxyphenylphenyliodonium salt and/or bis(t-butylphenyl)iodonium salt. Preferred alkoxyphenylphenyliodonium salts include 4-octyloxyphenyl phenyliodonium hexafluoroantimonate and 4-methoxyphenyl phenyliodonium hexafluoroantimonate. The photoimageable composition is particularly suited for producing high aspect ratio microstructures.

25 Claims, 5 Drawing Sheets

1 4-methoxyphenyl phenyliodonium hexafluoroantimonate MPI-HFA, MK

2 4-methoxyphenyl phenyliodonium camphorsulfonate MPI-CS, MK

3 4-methoxyphenyl phenyliodonium trifluoromethanesulfonate MPI-CS, MK

4 Bis t-butylphenyl phenyliodonium perfluorobutanesulfonate MPI-PFBS, MK

5 Bis t-butylphenyl phenyliodonium hexafluoroantimonate BBI-HFA, MK

6 Bis t-butylphenyl phenyliodonium trifluoromethane sulfonato methide BBI-M, 3M

U.S. PATENT DOCUMENTS

| | | |
|---|---|---|
| 6,235,448 B1 | 5/2001 | Lee et al. |
| 6,245,478 B1 | 6/2001 | Uetani et al. |
| 6,245,849 B1 | 6/2001 | Morales |
| 6,261,724 B1 | 7/2001 | Bula et al. |
| 6,261,738 B1 | 7/2001 | Asakura et al. |
| 6,268,436 B1 | 7/2001 | Chen et al. |
| 6,280,090 B1 | 8/2001 | Stephens et al. |
| 6,296,984 B1 | 10/2001 | Gabor et al. |
| 6,645,696 B1 * | 11/2003 | Simison et al. ............. 430/324 |
| 2002/0055059 A1 * | 5/2002 | Nishimura et al. ...... 430/270.1 |

* cited by examiner

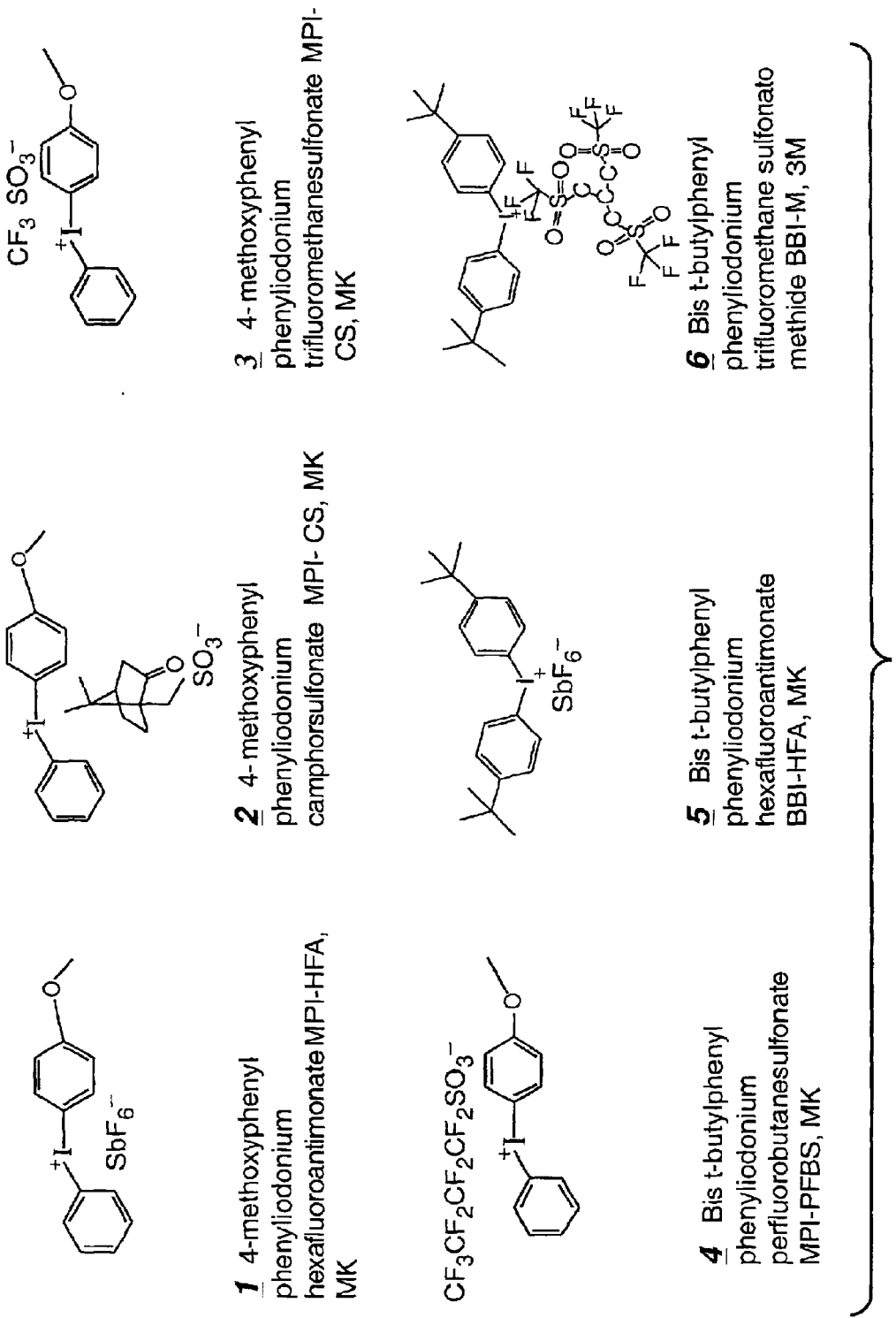
FIG._1A

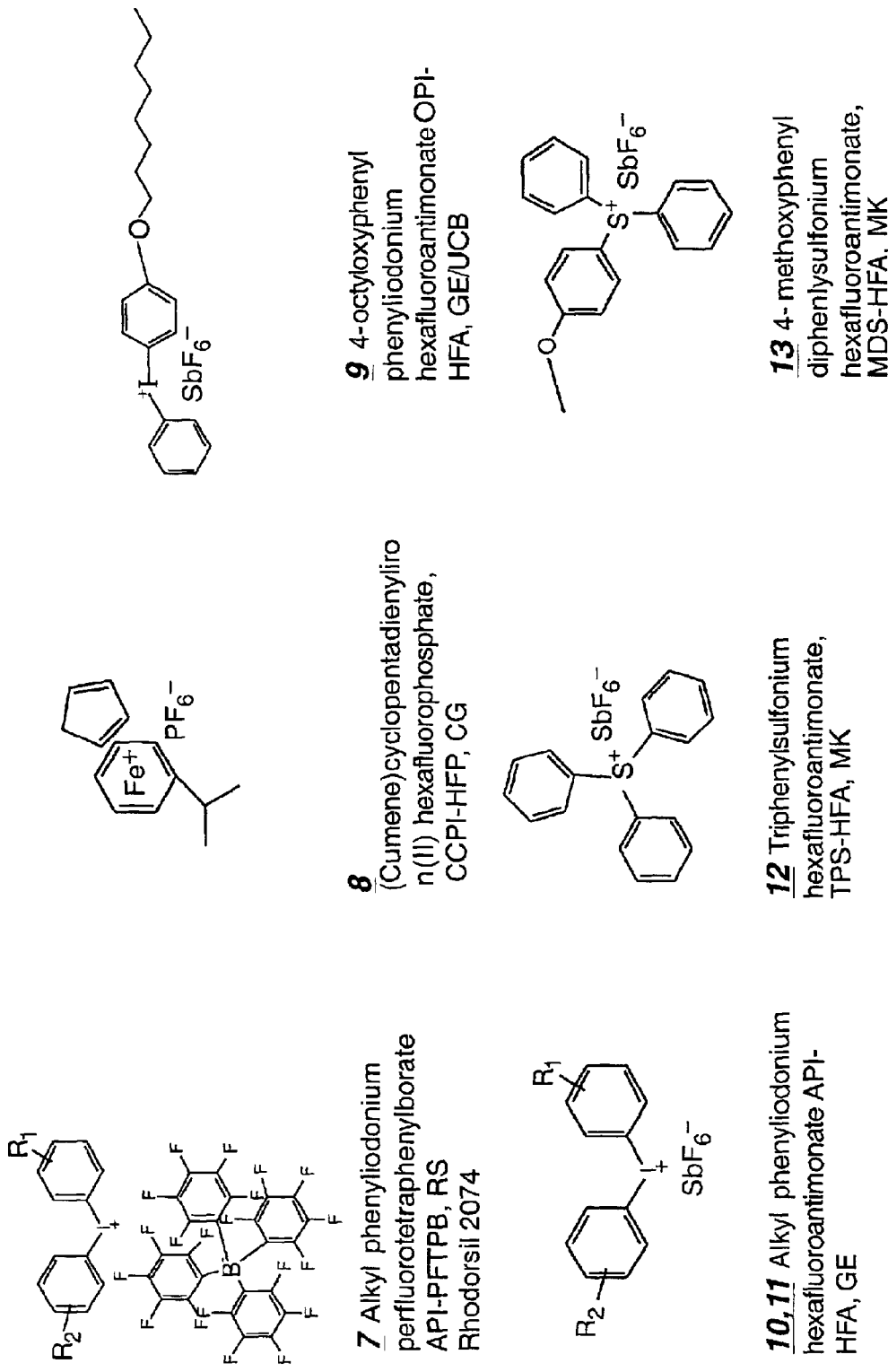
FIG._1B

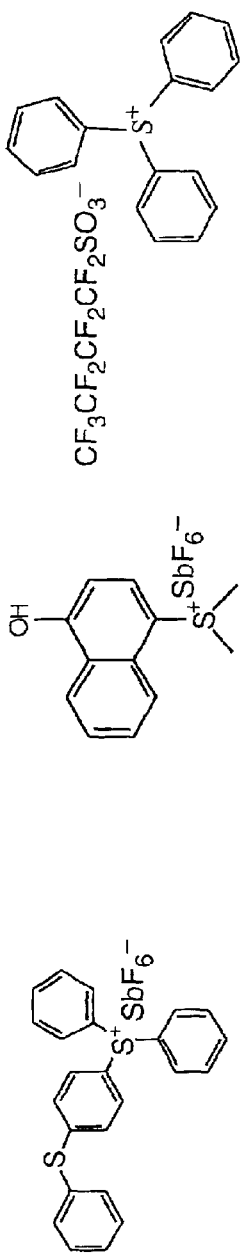
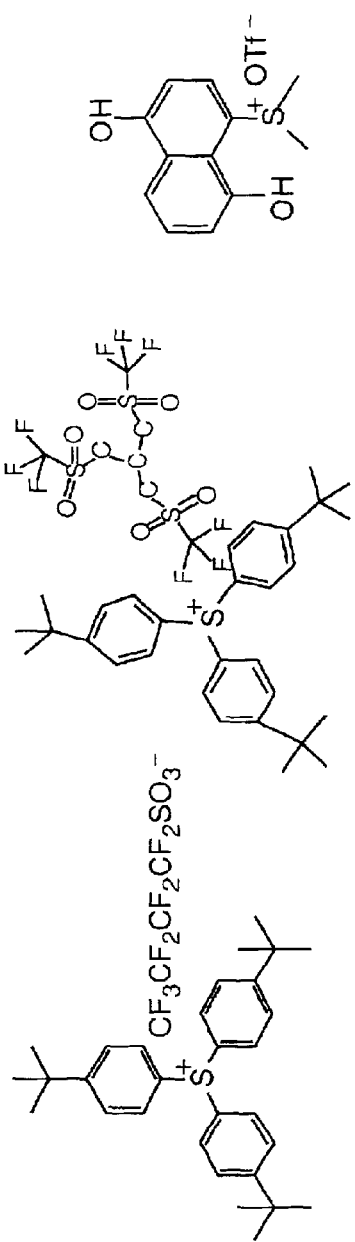
FIG._1C

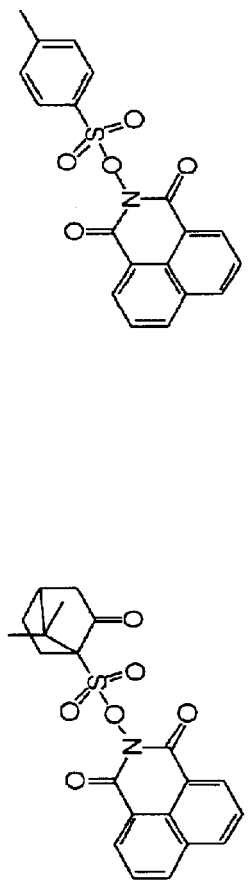
FIG._1D

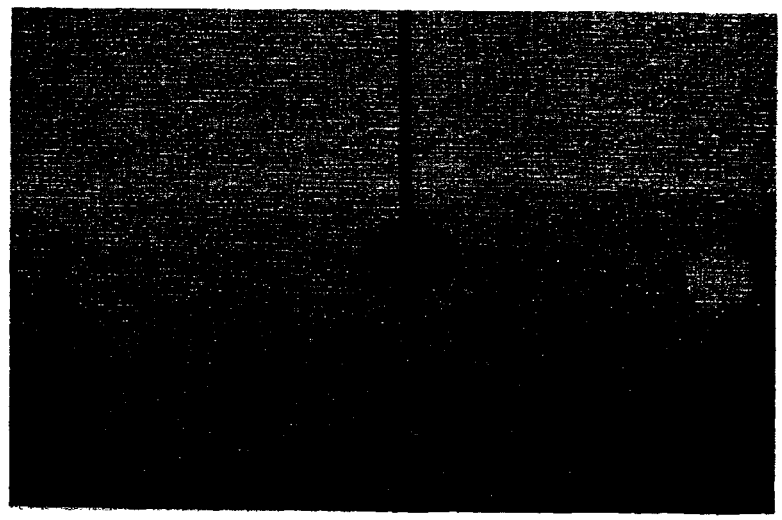
FIG._2

PHOTOIMAGEABLE COMPOSITION

This invention was made with Government support under Contract No. DE-AC04-94AL85000 awarded by the U.S. Department of Energy to Sandia Corporation. The Government has certain rights to the invention.

FIELD OF THE INVENTION

The present invention is directed to photoimageable compositions of improved composition that exhibit superior resolution. The invention is also directed to methods of fabricating microstructure metal parts using the photoimageable composition and particularly to fabricating microstructures having non-linear features.

BACKGROUND OF THE INVENTION

There are a variety of applications for which thick-film lithography may prove advantageous or even necessary. For instance, thick-film lithography may be used as a plating mold to create metal parts as in the LIGA process. Additionally, there may be applications in thick microelectro mechanical systems or lithographically defined analytical systems such as, for example, chromatography columns or mass spectrometers. Typically, photoresist films greater than 50–100 microns thick are exposed with a synchrotron source; the hard x-rays produced assure good transmission within the photoresist and low diffraction from the mask. In addition, the low run-out from synchrotron sources produces sharp side walls, but synchrotron sources are scarce and expensive. Moreover, long exposure times on the order of hours to days are typical.

Diazonapthoquinone/novolac (DNQ/novolac) resists that are exposed with ultraviolet radiation are used in microcircuit manufacturing. However, these materials suffer from several drawbacks when used in thick ($\leq 50 \mu m$) films. DNQ produces nitrogen gas upon exposure which phase separates prior to diffusing from thick films to create bubbles. Novolac materials form highly absorbing quinones, and the DNQ direct photolysis mechanism typically results in photoresist formulations exhibiting low transmittance. Careful bake steps are required to remove the casting solvent to avoid thermally inducing reactions with the DNQ. In addition, DNQ requires water for proper formation of the soluble, photoproduced acid which leads to requiring long reabsorption times after the initial post-apply bake (PAB). Finally, novolac materials have a tendency to crack, which is particularly problematic for thick films.

A chemically-amplified negative resist, available from MicroChem Corp., Newton, Mass., under the tradename SU-8, circumvents many of these problems. The resist includes monomers and oligomers of bisphenol A, which have been quantitatively protected with glycidyl ether, and a photoacid generator (PAG). UV exposure creates a strong acid which cationically crosslinks the oligomers during a post-exposure bake (PEB) step to form a highly crosslinked network. The resist exhibits high transmission, creates no gas during exposure, and is thermally stable. UV exposures of the resist are typically on the order of minutes, and the cured product provides the best imaging resolution of known resists. However, drawbacks of this resist include solvent development, shrinkage of the cured material, and when used in very thick films, absorption of radiation can result in degraded sidewall profiles. These drawbacks result in poor resolution. The cured resist is also difficult to remove.

SUMMARY OF THE INVENTION

The invention is based in part on the demonstration that the use of alkoxyphenylphenyliodonium salt and/or bis(t-butylphenyl)iodonium salt photoacid generators in a photoimageable composition improves resolution.

In one aspect, the invention is directed to a photoimageable composition that includes:
  (a) a multifunctional polymeric epoxy resin that is dissolved in an organic solvent wherein the epoxy resin comprises oligomers of bisphenol A that are quantitatively protected by glycidyl ether and wherein the oligomers have an average functionality that ranges from about 3 to 12; and
  (b) a photoacid generator comprising an alkoxyphenylphenyliodonium salt and/or bis(t-butylphenyl) iodonium salt.

Preferred photoacid generators include 4-octyloxyphenyl phenyliodonium hexafluoroantimonate, 4-methoxyphenyl phenyliodonium hexafluoroantimonate, bis(t-butylphenyl) iodonium hexafluoroantimonate, and methide salts of these.

In another aspect, the invention is directed to a method of fabricating microstructures that includes the steps of:
  (a) forming a layer of photoimageable composition on a substrate surface wherein the photoimageable composition comprises:
    (i) a multifunctional polymeric epoxy resin that is dissolved in an organic solvent wherein the epoxy resin comprises oligomers of bisphenol A that are quantitatively protected by glycidyl ether and wherein the oligomers have an average functionality that ranges from about 3 to 12; and
    (ii) a photoactive compound comprising an alkoxyphenylphenyliodonium salt and/or bis(t-butylphenyl) iodonium salt;
  (b) exposing the layer of photoimageable composition to a pattern of radiation which produces a catalyst capable of changing the photoimageable composition's susceptibility to a developer; and
  (c) applying a developer to remove nonexposed portions of the photoimageable compound which are susceptible to the developer.

In a further aspect, the invention is directed to a method of fabricating a metal structure that includes the steps of:
  (a) forming a layer of photoimageable composition on a substrate surface wherein the photoimageable composition comprises:
    (i) a multifunctional polymeric epoxy resin that is dissolved in an organic solvent wherein the epoxy resin comprises oligomers of bisphenol A that is quantitatively protected by glycidyl ether and wherein the oligomers have an average functionality that ranges from about 3 to 12; and
    (ii) a photoacid generator comprising an alkoxyphenylphenyliodonium salt and/or bis(t-butylphenyl) iodonium salt;
  (b) exposing the layer of photoimageable composition to a pattern of radiation which changes the photoimageable composition's susceptibility to a developer;
  (c) applying a developer to remove nonexposed portions of the photoimageable composition which are susceptible to the developer to create a mold area within an exposed portions of the photoimageable composition;
  (d) depositing a metal into the mold area; and
  (e) removing the exposed photoimageable composition to yield the metal structure.

BRIEF DESCRIPTION OF THE DRAWINGS

FIGS. 1A, 1B, 1C, and 1D show the structures of 23 photoinitiators that were tested.

FIG. 2 is a SEM photograph of a trench that is formed in resist material.

DESCRIPTION OF PREFERRED EMBODIMENT

Photoimageable compositions of the present invention generally comprise (a) a multifunctional polymeric epoxy resin that is dissolved in an organic solvent wherein the epoxy resin comprises oligomers of bisphenol A that are quantitatively protected by glycidyl ether and wherein the oligomers have an average functionality that ranges from about 3 to 12 and preferably about 8; and (b) a photoacid generator comprising an alkoxyphenylphenyliodonium salt and/or bis(t-butylphenyl)iodonium salt.

Preferably, the multifunctional polymeric epoxy resin comprises a bisphenhol A novolac glycidyl ether having the following structure (I):

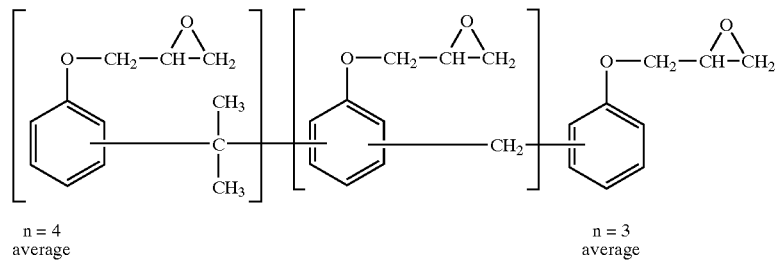

n = 4 average n = 3 average

The multifunctional polymeric epoxy resin typically comprises about 80% to 99% and preferably about 93% to 99% by weight of the photoimageable composition.

A photoactive compound (PAC) is a compound that undergoes a photochemical transformation upon absorption of photon. Photoacid generators (PAG) and photobase generators generate upon absorption of a photon an acid or base, respectively. A PAG has a chromophore and an acid salt. The salt can be any suitable anion, but preferably is an anion selected from tetrafluoroborate, hexafluorophosphate, hexafluoroarsenate, hexafluoroantimonate, trifluoromethane sulfonate, perfluorotetraphenylborate or fluorinated methides.

Photoimageable compositions of the present invention employ one or more photoacid generators wherein the chromophore comp rises an alkoxyphenylphenyl iodonium and/or bis(t-butylphenyl)iodonium cation. The PAC typically comprises about 1% to 10% and preferably about 1% to 6% by weight based on the weight of the multi functional polymeric epoxy resin.

Prior to discussing this invention in further detail, the following terms will first be defined.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkyl" refers to monovalent alkyl groups preferably having from 1 to 20 carbon atoms and more preferably 1 to 12 carbon atoms. This term is exemplified by groups such as methyl, ethyl, n-propyl, isopropyl, n-butyl, iso-butyl, n-hexyl, and the like.

The term "alkenyl" refers to alkenyl groups preferably having from 1 to 20 carbon atoms and more preferably 1 to 12 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), isopropenyl (—C(CH$_3$)=CH$_2$), and the like.

The term "alkynyl" refers to alkynyl groups preferably having from 1 to 20 carbon atoms and more preferably 1 to 12 carbon atoms and having at least 1 and preferably from 1–2 sites of alkynyl unsaturation. Preferred alkynyl groups include ethynyl (—C≡CH), propargyl (—CH$_2$C—CH) and the like.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

The term "cycloalkenyl" refers to cyclic alkenyl groups of from 4 to 8 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "methide" refers to (R$_f$SO$_2$)$_3$C$^-$ wherein each R$_f$ is independently selected from the group consisting of highly fluorinated or perfluorinated alkyl or fluorinated aryl radicals. The methides may also be cyclic, when a combination of any two R$_f$ groups are linked to form a bridge. The R$_f$ alkyl chains may contain from 1–20 carbon atoms, with 14 carbon atoms preferred. The R$_f$ alkyl chains may be straight, branched, or cyclic and preferably are straight. When R$_f$ is or contains a cyclic structure, such structure preferably has 5 or 6 ring members, 1 or 2 of which can be heteroatoms. The alkyl radical R$_f$ is also free of ethylenic or other carbon—carbon unsaturation: e.g., it is a saturated aliphatic, cycloaliphatic or heterocyclic radical.

By "highly fluorinated" is meant that the degree of fluorination on the chain is sufficient to provide the chain with properties similar to those of a perfluorinated chain. More particularly, a highly fluorinated alkyl group will have more than half the total number of hydrogen atoms on the chain replaced with fluorine atoms. Although hydrogen atoms may remain on the chain, it is preferred that all hydrogen atoms be replaced with fluorine to form a perfluoroalkyl group, and that any hydrogen atoms beyond at least half replaced with fluorine that are not replaced with fluorine be replaced with bromine and or chlorine. It is more preferred that at least two out of three hydrogens on the alkyl group be replaced with fluorine, still more preferred that at least three of four hydrogen atoms be replaced with fluorine and most preferred that all hydrogen atoms be replaced with fluorine to form a perfluorinated alkyl group.

The fluorinated aryl radicals of the methide structure may contain from 6 to 22 ring carbon atoms, preferably 6 ring carbon atoms, where at least one, and preferably at least two, ring carbon atoms of each aryl radical is substituted with a fluorine atom or a highly fluorinated or perfluorinated alkyl radical as defined above, e.g., $CF_3$. Suitable methide anions are further described in U.S. Pat. No. 5,554,664 which is incorporated herein.

Preferably, the alkoxyphenylphenyliodonium salt has the following structure:

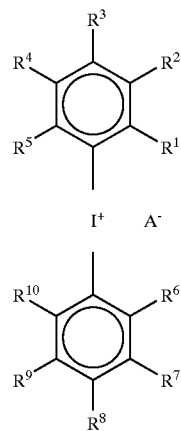

wherein each of $R^1$, $R^2$, $R^3$, $R^4$, $R^5$, $R^6$, $R^1$, $R^9$, and $R^{10}$ is independently selected from the group consisting of —H, alkyl-O—, alkenyl-O—, cycloalkyl-O—, cycloalkenyl-O—, and alkynyl-O—, with the proviso that not all are —H; and A is a suitable anion.

In a preferred embodiment, $R^3$ and/or $R^8$ are alkyl-O— and the remaining substituents are hydrogen. A preferred alkyl-O— is n-octyl-O—. In another preferred embodiment, $R^3$ and $R^8$ are t-butyl and remaining substituents are hydrogen. Preferred anions include, for example, tetrafluoroborate, hexafluorophosphate, hexafluoroarsenate, hexafluoroantimonate, trifluoromethane sulfonate, perfluorotetraphenyl borate or fluorinated methides.

Optionally the photoimageable composition can also include an amine that is selected from the group consisting of triisobutylamine (TIBA), 1,8-bis(dimethylamino) naphthalene 1,8-bis(dimethylamino)naphthalene (also known as PROTON SPONGE™) (PS), 2,2'-diazabicyclo [2.2.2]octane (DABCO) and mixtures thereof. The amount of amine used is about 0.1 mol % to 25 mol % and preferably about 1 mol % to 15 mol % based on the moles of PAC present. The presence of the amine reduces process bias.

The organic solvent comprises any suitable solvent for the components set forth above. Typical solvents include, for example, propylene glycol methyl ether acetate (PGMEA), γ-butyrolactone and cyclopentanone. The solvent typically comprises about 10% to 80% and preferably about 25% to 50% by weight of the photoimageable composition.

The photoimageable composition of the present invention can be formulated by adding the PAC to a polymer mixture. The photoimageable composition of the present invention can be employed in the same manner as conventional negative resist compositions but with improved results. For example, the photoimageable composition can be applied (e.g., spun) onto a substrate surface; the thickness of the film is determined by the composition's viscosity. A post-apply bake (PAB) step removes solvent from the film after coating. The photoimaging mechanism is initiated when radiation (e.g., ultraviolet radiation) is directed to regions of film to cause the production of photoacids or photobases which act as a catalyst in the subsequent crosslinking reaction that takes place during the post-exposure bake (PEB) step. The photoimageable composition is referred to as a negative photoimageable composition in that the exposed portions are not susceptible to removal by the developer while the unexposed composition portions are.

Photoimageable compositions of the present invention are particularly suited for making metal parts that have non-linear dimensions and/or high aspect ratios of from 0.1 to 70. In particular, the compositions can be employed to manufacture microstructures or microcomponents which refer to three-dimensional solid structures whose critical features, height, width (or diameter) or length is less than about 100 microns, i.e., at least one dimension of the three-dimensional structure is less than about 100 microns. It has been demonstrated that the inventive photoimageable composition significantly improves the resolution associated with prior art resists.

Microstructures can be fabricated using LIGA processes. "LIGA" is a German acronym for a process involving X-ray lithography, electroplating, and plastic molding. Conventional sources of radiation including X-ray and ultraviolet radiation can be used with the inventive photoimageable composition. A typical LIGA process involves applying a layer of photoimageable composition onto a suitable substrate. The thickness of the layer is typically equal to or greater than the desired height of the microstructure. The photoimageable composition is then positioned behind a patterned mask and exposed to a collimated ultraviolet radiation. After exposure, a developer dissolves the non-irradiated areas. The resulting template or mold is then used to electroplate microstructures on the electroplating base. When electroplating is completed, the wafer is planarized, and the remaining polymer layer is removed to produce the microstructure.

One embodiment of photoimageable composition of the present invention can be formulated by adding appropriate photoacid generator(s) to a polymer formulation that is commercially available as SU8 R50 from MicroChem Corp. This commercial composition contains a resist mixture of monomers and oligomers of bisphenol A that are quantitatively protected by glycidyl ether and has an average functionality of 8 as represented by structure (I) shown above. The solids content of the resist mixture is about 69% by weight. The composition SU8 R50 does not contain a photoacid generator. While the invention will be illustrated using SU8 R50 it is understood that the photoacid generators of the present invention will also improve resolution in other photoimageable compositions containing the requisite components as defined above.

EXPERIMENTAL

Various photoimageable compositions containing different photoacid generators (PAGs) were prepared and tested to demonstrate the superior properties (i.e., resolution) attained by using the alkoxyphenylphenyliodonium salt and/or bis(t-butylphenyl)iodonium salt. The photoimageable compositions with the PAGs were formulated with SU8 R50 as the nominal composition. The structures and acronyms of the PAGs tested are shown in FIGS. 1A, 1B, 1C and 1D. As noted in the figures, the PAGs were obtained from commercial sources including: Midori Kagaku Ltd. (MK) (Tokyo, Japan), Toyo Gosei (TGK) (Tokyo, Japan), GE Silicones Division (GE), UCB Chemicals, 3M, Rhodia Silicones (RS), and Aldrich via Ciba Geigy Specialty Chemicals (CG). Typically, a mixture of 2% PAG to SU8 R50 solids was rolled overnight on a hematology mixer. Samples which did not dissolve easily were rolled overnight at about 65° C.

Imaging experiments were done with a standard resolution test pattern. The pattern contains both tones of elbows, isolated square posts, isolated supported and unsupported lines, and "bullseye" patterns. The features range in size from 80, 50, 40, 35, 30, 25, 20, 17.5, 15, 12.5, 10, 8, 6, 5, 4, 3 and 2 μm. Formulations were spun at 1500 rpm for 15 sec., baked at 80° C. for 5 min. and then subject to an edge bead removal with streaming acetone at approximately 900 rpm. The post-apply bake (PAB) step was from room temperature (RT) to 95° C. at 2° C./min., hold for 7 min., and then cool to RT at 1° C./min. Exposure was done with broadband radiation (about 330–450 nm) in hard or soft contact on a Karl Suss MA/BA 6 aligner with reported doses measured at 365 nm. Four sites per wafer were exposed. Post-exposure bake (PEB) was done from 65° C. to 85° C. at 2° C./min., hold for 10 min., and then decrease at 1° C./min. to RT. Development was immersion in a crystallization dish with very gentle to no agitation at 3 times the clearing time for the bulk fields.

After processing, the wafers were inspected with an optical microscope for resolution and other detrimental effects such as cracking, peeling, etc. If appropriate, another wafer was typically exposed to get a more accurate dose. Particularly promising PAGs were formulated with several different concentrations and conditions for additional testing.

The following table 1 shows the compiled results for the PAG experiments.

TABLE 1

| Number | Dose (mJ/cm$^2$) | Imaging Comments |
| --- | --- | --- |
| 1 | 600 | Looked very good. High resolution, some cracking. |
| 2 | >>6000 | No latent image even at 6000. |
| 3 | 10,600 | Showed latent image at 6000, where 2 did not, images poor. Only 100 μm OK. Some dewetting in two layer experiment. 3.7 wt. % |
| 4 | >9000 | Horrible images, exceedingly slow |
| 5 | 6000 | Slow, lots of cracking, but resolution very good. |
| 6 | 1600 | Images quite good, but not as sharp as 5, much faster though. |
| 7 |  | Moderate doses, but lines sloped, pyramidal. |
| 8 |  | Lots of cracking, dose pretty good, images pretty good, but clearly inferior to 1, 9 |
| 9 | 1700 | Excellent images. Good adhesion, low cracking. Follow up experiments consistently better imaging by several people. |
| 10 | 1500 | UV 9380 C Images are quite nice, but there are bubbles and cracks everywhere. This formulation has ITX and a reactive diluent. It is quite impure. |
| 11 | DNE | UV9385 C Orange peeled and dewetted after PAB. Supposedly the same as UV 9380C but without the ITX. |
| 12 | 7200 | Decent resolution, but resist cracked and peeled badly. |
| 13 | >>4000 | Barely image at 4000, should be much higher dose than 12, |
| 14 | 1500 | Good images, but lots of cracking. Follow up experiment at high PAG [[conc]] concentration had peeling, images not as good as commercial material. |
| 15 | 1100 | Reasonable resolution, but dewetting was quite bad. |
| 16 | >>5000 |  |
| 17 | >>5000 | Same as 16 |
| 18 | >12,000 | Very slow even with fast acting acid. |
| 19 |  | Did not dissolve in SU-8/solvent solution. |
| 20 | >>1600 | Expect that the acid is not strong enough. |
| 21 |  | Phase separation in solid. |
| 22 |  | Did not dissolve in SU-8/solvent solution |
| 23 | >>3400 |  |
| SU-8 | >800 | Commercial formulation shows good resolution. Other formulations qualitatively compared to this formulation. |

There are three major conclusions from Table 1. The first is that only certain acids appear to be of sufficient "strength" to catalyze the epoxy reaction for imaging SU-8. While certain acids may catalyze epoxy reactions in general, for imaging, the resultant crosslinked film must withstand the development step without swelling, cracking, delaminating, etc. PAGs 1–4 are a direct comparison of the affect of the acid generated if we assume that the chromophore alone determines acid generation efficiency. Also, 5 vs. 6, 12 vs. 16, and PAGs 7 and 8 yield information on the type of acid required. It is clear from the homologues 1–4 that the hexafluoroantimonate is a particularly active acid, that the perfluorobutane sulfonate is somewhat active but slow and results in poor imaging and that the others are not active enough to reasonably crosslink the material at these conditions. Comparing PAGs 1 and 6 shows that the methide PAG appears to be significantly more active than even the hexafluoroantimonate. Comparing 12 and 16 confirm that the hexafluoroantimonate is considerably more active than the perfluorobutane sulfonate. PAGs 7 shows that the perfluorinated tetraphenyl borate is sufficiently strong as well. However, since the material is a formulated commercial product, it cannot be ruled out that other photoactive sensitizers are present. Finally, the hexfluorophosphate acid generated from PAG 8 is also sufficiently strong to catalyze the reaction. This is similar to the known work that the hexafluorophosphate analogue to the PAG used in the commercial SU-8 formulation (a hexafluoroantimonic acid generated from a mixture of triphenylsulfonium salts) is also capable of catalyzing the reaction sufficient for imaging though with some loss of resolution. The failure of formulations made from PAGs 20 and 23 could be entirely due to their weak generated acids, as both generate acids that are considerably weaker than the perfluoroalkane sulfonate counterparts.

It is clear that only some types of acids can effectively crosslink the SU-8 sufficient to withstand the solvent development step. It is not clear exactly why the hexafluoroantimonate acid creates such high resolution patterns, though its reactivity must be considered important. However, it is also clear that the methide acid is considerably faster but did not seem to provide as good a resolution at least with the bis t-butylphenyl iodonium chromophore.

Another significant conclusion from the data can be obtained by considering only the chromophore. PAGs 1, 5, 8, 9–15 all generate hexafluoroantimonic acid. The series provides insight into the mechanism of acid generation in SU-8 polymer. All of the iodonium chromophores shown have particularly low absorbance in the wavelength range of interest. However, it is known that the iodonium compounds are more susceptable to radiationless energy transfer from the matrix to the PAG, so they appear to be far more sensitive than the sulfonium counterparts. In particular, the alkoxyphenylphenyliodonium chromophore produces particularly fast photoresists in this matrix and both PAG 1 and 9 show excellent images. While the alkoxyphenylphenyliodonium chromophore shows red shifted absorbance relative to the bis(t-butyl)phenyl analogue, the alkoxyphenylphenyliodonium chromophores themselves do not absorb heavily in the wavelengths of interests (330 nm and longer wavelengths are the only ones that transmit through the optics and mask). However, it has been determined experimentally that the alkoxyphenyl phenyliodonium chromophores are more likely to receive energy from the matrix than their alkyl phenyl counterparts. One very significant advantage of the alkoxyphenyl phenyl iodonium chromophores, then, is the ability to print extremely thick structures. This arises from the absorbance of the entire formulation being low, while maintaining adequate photospeed for throughput considerations. PAGs 7 and 10, however, show that the alkylphenylphenyliodonium salts are capable of reasonably high sensitivity, though these commercial formulations are likely sensitized with compounds such as isopropyl-9H-thioxanthen-9-one (ITX). The sensitizers may be useful at boosting photospeed but will contribute to the overall absorbance of the film, and hence could limit the total thickness of the parts.

PAGs 12, 14, and 15 show that it is likely that the sulfonium counterparts require direct absorption for acid to be released. Both PAGs 14 and 15 have appreciable absorption in the wavelengths of interest and are reasonably fast. However, PAGs 12 and 13 are not highly absorbing and result in particularly slow resists. That sulfonium PAGs are more difficult to sensitize by their matrices has been shown elsewhere.

A third conclusion is that no particular structure is obviously affecting the other imaging requirements such as dewetting, adhesion, cracking of the film, etc. It is clear that there are several desirable features of the chromophore such as high transmission with good sensitivity afforded by the alkoxyphenyphenyliodonium chromophores. It is also clear that there are certain desirable acids such as the hexafluoroantimonate, methide and potentially the perflourinated borates, but unfortunately, the structure of the total PAG is not clearly correlated with improved imaging performance.

After initial experiments shown in Table 1, PAGs 1, 5, 6, and 9 were attempted several more times. PAGs 1 and 9 consistently produced very nice images without noticeable dewetting or adhesion problems, and had particularly cleanly developed patterns. PAG 5 has been used successfully on several occasions, but has shown with increasing PAG concentration to be somewhat susceptible to adhesion issues. Because PAG 9 is a cost-effective solution and shows less cracking than PAG 1 and commercial SU-8, it was selected for a variety of experiments. After consistently failing to produce acceptable shuttle patterns with the commercial SU-8, a resist with 3% OPI-HFA PAG (9) was prepared and shown to produce the patterns shown in FIG. 2. The 6.5 micron trench is approximately 105 microns thick. As shown, the resist has vertical sidewalls and clean trenches. The trenches as shown in FIG. 2 could not be cleared in regular SU-8 and there was also a bit of difficulty with the SU-8 with triisobutyl amine. The OPI-HFA has been used in films up to 1 mm thickness with results not obtained using commercially available SU-8.

Finally, the OPI-HFA PAG has been combined with TIBA to create an optimal formulation which has been used repeatedly in Ni, and Ni-alloy plating baths to create parts from the LIGA process.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A method of fabricating a microstructure, which defines a three-dimensional solid structure wherein at least one of its height, width, diameter or length is less than about 100 microns, that comprises the steps of:
    (a) forming a layer of photoimageable composition on a substrate surface wherein the photoimageable composition comprises:
        (i) a multifunctional polymeric epoxy resin that is dissolved in an organic solvent wherein the epoxy resin comprises oligomers of bisphenol A that are quantitively protected by glycidyl ether and wherein the oligomers have an average functionality that ranges from about 3 to 12; and
        (ii) a photoactive compound comprising an alkoxyphenylphenyliodonium salt and/or bis(t-butylphenyl) iodonium salt;
    (b) exposing the layer of photoimageable composition to a pattern of radiation which produces a catalyst capable of changing the photoimageable composition's susceptibility to a developer;
    (c) applying a developer to remove nonexposed portions of the photoimageable compound which are susceptible to the developer thereby creating a layer defining one or more open patterns therein wherein the one or more open patterns have non-linear dimensions; and
    (d) filling the one or more open patterns with a metal.

2. The method of claim 1 wherein the photoactive compound is an alkoxyphenylphenyliodonium salt.

3. The method of claim 1 wherein the photoactive compound is selected from the group consisting of 4-octyloxyphenyl phenyliodonium hexafluoroantimonate (OPI HFA), 4-methoxyphenyl phenyliodonium hexafluoroantimonate (MPI HFA), methide salts thereof and mixtures thereof.

4. The method of claim 1 wherein the multifunctional polymeric epoxy resin comprises a bisphenol A novolac glycidyl ether.

5. The method of claim 1 wherein step (b) comprises exposing the layer of photoimageable composition with a pattern of ultraviolet radiation.

6. The method of claim 1 wherein the amount photoactive compound present is about 1 to 12 parts by weight based on 100 parts by weight of the resin.

7. The method of claim 1 wherein the photoactive compound is 4-octyloxyphenyl phenyliodonium hexafluoroantimonate.

8. The method of claim 1 wherein the photoactive compound is 4-methoxyphenyl phenyliodonium hexafluoroantimonate.

9. The method of claim 1 wherein the photoactive compound is bis(t-butylphenyl)iodonium hexafluoroantimonate or methide salts thereof.

10. The method of claim 1 wherein the oligomers have an average functionality of about 8.

11. A method of fabricating a metal structure, which defines a three-dimensional solid structure wherein at least one of its height, width, diameter or length is less than about 100 microns, that comprises the steps of:
    (a) forming a layer of photoimageable composition on a substrate surface wherein the photoimageable composition comprises:
        (i) a multifunctional polymeric epoxy resin that is dissolved in an organic solvent wherein the epoxy resin comprises oligomers of bisphenol A that are quantitatively protected by glycidyl ether and wherein the oligomers have an average functionality that ranges from about 3 to 12; and
        (ii) a photoacid generator comprising an alkoxyphenylphenyliodonium salt and/or bis(t-butyphenyl) iodonium salt;
    (b) exposing the layer of photoimageable composition to a pattern of radiation which changes the photoimageable composition's susceptibility to a developer;

(c) applying a developer to remove nonexposed portions of the photoimageable composition which are susceptible to the developer to create a mold area within an exposed portion of the photoimageable composition;

(d) depositing a metal into the mold area; and (e) removing the exposed photoimageable composition to yield the metal structure which has non-linear dimensions.

12. The method of claim 11 wherein the photoacid generator is an alkoxyphenylphenyliodonium salt.

13. The method of claim 11 wherein the photoacid generator is selected from the group consisting of 4-octyloxyphenyl phenyliodonium hexafluoroantimonate (OPI HFA), 4-methoxyphenyl phenyliodonium hexafluoroantimonate (MPI HFA), methide salts thereof, and mixtures thereof.

14. The method of claim 11 wherein the multifunctional polymeric epoxy resin comprises a bisphenol A novolac glycidyl ether.

15. The method of claim 11 wherein step (b) comprises exposing the layer of photoimageable composition with a pattern of ultraviolet radiation.

16. The method of claim 11 wherein the metal structure formed has a nonlinear surface.

17. The method of claim 11 wherein the metal structure formed has a curved surface.

18. The method of claim 11 wherein the amount photoacid generators present is about 1 to 12 parts by weight based on 100 parts by weight of the resin.

19. The method of claim 11 wherein the photoacid generator is 4-octyloxyphenyl phenyliodonium hexafluoroantimonate.

20. The method of claim 11 wherein the photoacid generator is 4-methoxyphenyl phenyliodonium hexafluoroantimonate.

21. The method of claim 11 wherein the photoacid generator is bis(t-butylphenyl)iodonium hexafluoroantimonate or methide salts thereof.

22. The method of claim 11 wherein the oligomers have an average functionality of about 8.

23. A method of fabricating microstructures that comprises the steps of:

(a) forming a layer of photoimageable composition on a substrate surface wherein the photoimageable composition comprises:

(i) a multifunctional polymeric epoxy resin that is dissolved in an organic solvent wherein the epoxy resin comprises oligomers of bisphenol A that are quantitively protected by glycidyl ether and wherein the oligomers have an average functionality that ranges from about 3 to 12; and (ii) a photoactive compound comprising 4-methoxyphenyl phenyliodonium hexafluoroantimonate;

(b) exposing the layer of photoimageable composition to a pattern of radiation which produces a catalyst capable of changing the photoimageable composition's susceptibility to a developer; and (c) applying a developer to remove nonexposed portions of the photoimageable compound which are susceptible to the developer.

24. A method of fabricating a metal structure, which are three-dimensional solid structures wherein at least one of its height, width, diameter or length is less than about 100 microns, that comprises the steps of:

(a) forming a layer of photoimageable composition on a substrate surface wherein the photoimageable composition comprises:

(i) a multifunctional polymeric epoxy resin that is dissolved in an organic solvent wherein the epoxy resin comprises oligomers of bisphenol A that are quantitatively protected by glycidyl ether and wherein the oligomers have an average functionality that ranges from about 3 to 12; and (ii) a photoacid generator comprising 4-methoxyphenyl phenyliodonium hexafluoroantimonate;

(b) exposing the layer of photoimageable composition to a pattern of radiation which changes the photoimageable composition's susceptibility to a developer;

(c) applying a developer to remove nonexposed portions of the photoimageable composition which are susceptible to the developer to create a mold area within an exposed portion of the photoimageable composition;

(d) depositing a metal into the mold area; and (e) removing the exposed photoimageable composition to yield the metal structure.

25. A method of fabricating a metal structure that comprises the steps of:

(a) forming a layer of photoimageable composition on a substrate surface wherein the photoimageable composition comprises:

(i) a multifunctional polymeric epoxy resin that is dissolved in an organic solvent wherein the epoxy resin comprises oligomers of bisphenol A that are quantitatively protected by glycidyl ether and wherein the oligomers have an average functionality that ranges from about 3 to 12; and (ii) a photoacid generator comprising bis(t-butylphenyl)iodonium hexafluoroantimonate or methide salts thereof;

(b) exposing the layer of photoimageable composition to a pattern of radiation which changes the photoimageable composition's susceptibility to a developer;

(c) applying a developer to remove nonexposed portions of the photoimageable composition which are susceptible to the developer to create a mold area within an exposed portion of the photoimageable composition;

(d) depositing a metal into the mold area; and (e) removing the exposed photoimageable composition to yield the metal structure.

* * * * *

UNITED STATES PATENT AND TRADEMARK OFFICE
CERTIFICATE OF CORRECTION

PATENT NO.     : 6,858,378 B1                                      Page 1 of 1
DATED          : February 22, 2005
INVENTOR(S)    : Dentinger et al.

It is certified that error appears in the above-identified patent and that said Letters Patent is hereby corrected as shown below:

<u>Title page,</u>
Item [75], Inventors, second inventor's last name should be corrected to read
-- Krafcik --.

Signed and Sealed this

Twenty-fourth Day of May, 2005

JON W. DUDAS
*Director of the United States Patent and Trademark Office*